United States Patent
Mann et al.

(10) Patent No.: US 9,288,990 B2
(45) Date of Patent: Mar. 22, 2016

(54) SYNERGISTIC WEED CONTROL FROM APPLICATIONS OF PENOXSULAM AND PETHOXAMID

(71) Applicant: Dow AgroSciences, LLC, Indianapolis, IN (US)

(72) Inventors: Richard Kevin Mann, Franklin, IN (US); Kirupanandam Ramesh Babu, Maharashtra (IN); Peter Nagy, Biot (FR)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/206,459

(22) Filed: Mar. 12, 2014

(65) Prior Publication Data
US 2014/0274711 A1    Sep. 18, 2014

Related U.S. Application Data

(60) Provisional application No. 61/787,155, filed on Mar. 15, 2013.

(51) Int. Cl.
*A01N 43/90* (2006.01)
*A01N 37/20* (2006.01)

(52) U.S. Cl.
CPC ............... *A01N 43/90* (2013.01); *A01N 37/20* (2013.01)

(58) Field of Classification Search
CPC ............................. A01N 43/90; A01N 37/20
USPC ........................................................ 504/136
See application file for complete search history.

(56) References Cited

U.S. PATENT DOCUMENTS

| | | | |
|---|---|---|---|
| 5,858,924 A | 1/1999 | Johnson et al. | |
| 7,314,849 B2 | 1/2008 | Balko et al. | |
| 7,432,227 B2 | 10/2008 | Balko et al. | |
| 2002/0055435 A1 | 5/2002 | Baltruschat et al. | |
| 2003/0069137 A1 | 4/2003 | Almsick et al. | |
| 2004/0102321 A1 | 5/2004 | Feucht et al. | |
| 2006/0183637 A1* | 8/2006 | Loughner et al. | 504/101 |
| 2010/0099564 A1 | 4/2010 | Hacker et al. | |
| 2011/0092367 A1 | 4/2011 | Griveau et al. | |
| 2011/0190135 A1 | 8/2011 | Mann et al. | |
| 2011/0190136 A1 | 8/2011 | Hufnagl et al. | |

FOREIGN PATENT DOCUMENTS

| | | |
|---|---|---|
| CN | 101647450 A * | 2/2010 |
| CN | 102132702 B | 1/2013 |
| EP | 0206251 B1 | 9/1988 |
| EP | 1313369 B1 | 5/2003 |
| EP | 2303022 B1 | 4/2011 |
| WO | 2011097187 A2 | 8/2011 |
| WO | 2012150333 A1 | 11/2012 |
| WO | 2012156304 A1 | 11/2012 |
| WO | 2013026811 A1 | 2/2013 |

OTHER PUBLICATIONS

Farm Chemical International, Crop Protection Database, "Penoxsulam" (2013).
Farm Chemical International, Crop Protection Database, "Pethoxamid" (2013).
Auriga Industries, "Satisfactory start to the Year: Roadshow Zurich," May 29, 2012, available at http://files.shareholder.com/downloads/ABEA-6J07WI/0x0x577389/da287e47-7c20-4e3d-bc2b-555f1ea75e4f/zurich_29052012_investorpresentation_final.pdf (accessed on Jun. 10, 2014).
International Search Report and Written Opinion issued Jun. 3, 2014, in related International Patent Application No. PCT/US2014/019555.
Tomlin, C. D. S., Ed., The Pesticide Manual: A World Compendium, "Penoxsulam," 15th ed., BCPC: Alton, 2009, pp. 874-875.
Tomlin, C. D. S., Ed., The Pesticide Manual: A World Compendium, "Pethoxamid," 15th ed., BCPC: Alton, 2009, pp. 881-882.

* cited by examiner

*Primary Examiner* — John Pak
*Assistant Examiner* — Andriae M Holt
(74) *Attorney, Agent, or Firm* — Michael R. Asam; Meunier Carlin & Curfman, LLC

(57) ABSTRACT

Disclosed herein are herbicidal compositions comprising a synergistic herbicidally effective amount of (a) penoxsulam, or an agriculturally acceptable salt thereof, and (b) pethoxamid, or an agriculturally acceptable salt thereof. Also disclosed herein are methods of controlling undesirable vegetation, which comprise applying to vegetation or an area adjacent the vegetation or applying to soil to prevent the emergence or growth of vegetation (a) penoxsulam, or an agriculturally acceptable salt thereof, and (b) pethoxamid, or an agriculturally acceptable salt thereof, wherein (a) and (b) are each added in an amount sufficient to produce a synergistic herbicidal effect.

18 Claims, No Drawings

SYNERGISTIC WEED CONTROL FROM APPLICATIONS OF PENOXSULAM AND PETHOXAMID

CROSS REFERENCE TO RELATED APPLICATIONS

This application claims the benefit of U.S. Provisional Application No. 61/787,155 filed Mar. 15, 2013, which is hereby incorporated herein by reference in its entirety.

FIELD OF THE DISCLOSURE

The present disclosure relates to herbicidal compositions comprising a synergistically herbicidal effective amount of (a) penoxsulam or an agriculturally acceptable salt thereof, and (b) pethoxamid or an agriculturally acceptable salt thereof. The present disclosure also relates to methods for controlling undesirable vegetation in corn, *sorghum* and other cereal crops.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) penoxsulam, or an agriculturally acceptable salt thereof, and (b) pethoxamid, or an agriculturally acceptable salt thereof, display a synergistic herbicidal effect when applied in combination.

Accordingly, the present disclosure relates to herbicidal compositions comprising a synergistic herbicidally effective amount of (a) penoxsulam, or an agriculturally acceptable salt thereof, and (b) pethoxamid, or an agriculturally acceptable salt thereof. The weight ratio of (a) to (b) can be from 1:500 to 1:10 (e.g., from 1:300 to 1:8.3, from 1:240 to 1:120).

In some embodiments, the composition further comprises an additional pesticide (e.g., mesotrione, or an agriculturally acceptable salt thereof). In some embodiments, the composition further comprises an agriculturally acceptable adjuvant or carrier.

The present disclosure also relates to methods of controlling undesirable vegetation, which comprise applying to vegetation or an area adjacent the vegetation or applying to soil to prevent the emergence or growth of vegetation (a) penoxsulam, or an agriculturally acceptable salt thereof and (b) pethoxamid, or an agriculturally acceptable salt thereof, wherein (a) and (b) are each applied in an amount sufficient to produce a synergistic herbicidal effect. In some embodiments, (a) and (b) are applied simultaneously or sequentially. In some embodiments, (a) and (b) are applied pre-emergence or post-emergence to the undesirable vegetation and the crop.

The undesirable vegetation can be a broadleaf weed, a grass weed, a sedge weed, or combinations thereof. In some embodiments, the undesirable vegetation includes common ragweed, common lamb's quarters, barnyard grass, canker root, annual mercury, common cocklebur, ladysthumb, and combinations thereof. The undesirable vegetation can be controlled in, for instance, corn, *sorghum* and other cereal crops.

In some embodiments, (a) is applied in an amount of from 1-50 grams of active ingredient per hectare (g ai/ha) (e.g., from 3-20 g ai/ha or 5-10 g ai/ha). In some embodiments, (b) is applied in an amount of from 500-1500 g ai/ha (e.g., from 750-1300 g ai/ha).

The description below sets forth details of one or more embodiments of the present disclosure. Other features, objects, and advantages will be apparent from the description and from the claims.

DETAILED DESCRIPTION

The present disclosure relates to herbicidal compositions comprising a synergistic herbicidally effective amount of (a) penoxsulam, or an agriculturally acceptable salt thereof, and (b) pethoxamid, or an agriculturally acceptable salt thereof. The present disclosure also relates to methods for controlling undesirable vegetation in corn.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

As used herein, "controlling undesirable vegetation" means preventing, reducing, killing, or otherwise adversely modifying the development of plants and vegetation. Described herein are methods of controlling undesirable vegetation through the application of certain herbicide combinations or compositions.

Penoxsulam

Compositions and methods of the present disclosure can include penoxsulam (i.e., 2-(2,2-difluoroethoxy)-N-(5,8-dimethoxy[1,2,4]triazolo[1,5-c]pyrimidin-2-yl)-6-trifluoromethyl)benzenesulfonamide) or an agriculturally acceptable salt thereof. Penoxsulam, shown below, is a triazolopyrimidine sulfonamide herbicide that provides broad-spectrum control of many annual, biannual, and perennial weeds. Penoxsulam, as well as methods of preparing penoxsulam, are known in the art. See, for example, U.S. Pat. No. 5,858,924 to Johnson, et al.

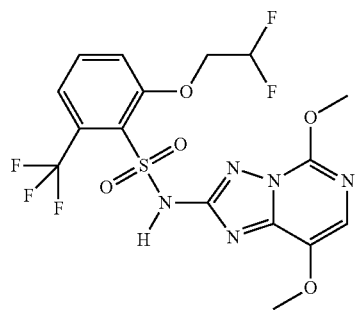 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam. Exemplary agriculturally acceptable salts of penoxsulam include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri (hydroxyethyl)ammonium, hydroxypropylammonium, di(hydroxypropyl)ammonium and tri(hydroxypropyl)ammonium salts, olamine salts, and diglycolamine salts.

Penoxsulam can be used to control broadleaf weeds in, for instance, rice, corn, *sorghum*, wheat, barley and other cereal crops, lawns (e.g., residential, industrial, and institutional), golf courses, parks, cemeteries, athletic fields, sod farms, tree and vine crops, range and pasture, rights-of-way, roadsides, and other crop and non-crop uses. Its herbicidal activity is described in The Pesticide Manual, Sixteenth Edition, 2012. Penoxsulam is or has been commercially available, for example, from Dow AgroSciences, LLC under the trademarks FENCER®, RICER®, VIPER®, CLIPPER®, SAPPHIRE®, GRASP®, and GRANITE®, and from SePRO Corporation under the trademark GALLEON®.

Penoxsulam or an agriculturally acceptable salt thereof can be applied to vegetation or an area adjacent the vegetation or applied to soil to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil to prevent the emergence or growth of vegetation in an amount of 1 gram of active ingredient per hectare (g ai/ha) or greater (e.g., 2 g ai/ha or greater, 3 g ai/ha or greater, 4 g ai/ha or greater, 5 g ai/ha or greater, 7.5 g ai/ha or greater, 10 g ai/ha or greater, 15 g ai/ha or greater, 20 g ai/ha or greater, 30 g ai/ha or greater, or 40 g ai/ha or greater). In some embodiments, the penoxsulam or agriculturally acceptable salt thereof is applied to vegetation or an area adjacent the vegetation or applied to soil to prevent the emergence or growth of vegetation in an amount of 50 g ai/ha or less (e.g., 40 g ai/ha or less, 30 g ai/ha or less, 20 g ai/ha or less, 15 g ai/ha or less, 10 g ai/ha or less, 7.5 g ai/ha or less, 5 g ai/ha or less, 4 g ai/ha or less, 3 g ai/ha or less, or 2 g ai/ha or less).

Penoxsulam can be applied to vegetation or an area adjacent the vegetation or applied to soil to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil to prevent the emergence or growth of vegetation in an amount of from 1-50 g ai/ha (e.g., from 2-40 g ai/ha, from 3-30 g ai/ha, from 4-20 g ai/ha, from 5-15 g ai/ha, or from 5-10 g ai/ha). In some embodiments, the penoxsulam or agriculturally acceptable salt thereof is applied to vegetation or an area adjacent the vegetation or applied to soil to prevent the emergence or growth of vegetation in an amount of less than 35 g ai/ha.

Pethoxamid

Compositions and methods of the present disclosure can include pethoxamid or an agriculturally acceptable salt thereof. Pethoxamid (i.e., 2-chloro-N-(ethoxyethyl)-N-(2-methyl-1-phenylprop-1-enyl)acetamide), shown below, is a chloroacetamide herbicide that can be used to control weeds in, for instance, corn and soybeans. Pethoxamid, as well as methods of preparing pethoxamid, are known in the art. See, for example, European Patent No. 206,251 to Kato, et al.

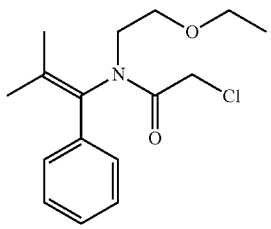 [SMILES: CCOCCN(C(=O)CCl)C(=C(C)C)c1ccccc1]

In some embodiments, pethoxamid can be provided as an agriculturally acceptable salt of pethoxamid. Exemplary agriculturally acceptable salts of pethoxamid include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri (hydroxyethyl)ammonium, hydroxypropylammonium, di(hydroxypropyl)ammonium and tri(hydroxypropyl)ammonium salts, olamine salts, and diglycolamine salts.

Its herbicidal activity is described in The Pesticide Manual, Sixteenth Edition, 2012. Pethoxamid is or has been commercially available, for example, under the trademarks SUCCESSOR® (by Cheminova A/S).

The pethoxamid or an agriculturally acceptable salt thereof can be used in an amount sufficient to induce a herbicidal effect. In some embodiments, the pethoxamid or agriculturally acceptable salt thereof is applied to vegetation or an area adjacent the vegetation or applied to soil to prevent the emergence or growth of vegetation in an amount of 500 grams of active ingredient per hectare (g ai/ha) or greater (e.g., 600 g ai/ha or greater, 700 g ai/ha or greater, 750 g ai/ha or greater, 800 g ai/ha or greater, 900 g ai/ha or greater, 1000 g ai/ha or greater, 1100 g ai/ha or greater, 1200 g ai/ha or greater, 1250 g ai/ha or greater, 1300 g ai/ha or greater, or 1400 g ai/ha or greater). In some embodiments, the pethoxamid or agriculturally acceptable salt thereof is applied to vegetation or an area adjacent the vegetation or applied to soil to prevent the emergence or growth of vegetation in an amount of 1500 g ai/ha or less (e.g., 1400 g ai/ha or less, 1300 g ai/ha or less, 1250 g ai/ha or less, 1200 g ai/ha or less, 1100 g ai/ha or less, 1000 g ai/ha or less, 900 g ai/ha or less, 800 g ai/ha or less, 750 g ai/ha or less, 700 g ai/ha or less, or 600 g ai/ha or less).

Pethoxamid can be applied to vegetation or an area adjacent the vegetation or applied to soil to prevent the emergence or growth of vegetation in an amount ranging from any of the minimum values described above to any of the maximum values described above. In some embodiments, the pethoxamid or agriculturally acceptable salt thereof is applied to vegetation or an area adjacent the vegetation or applied to soil to prevent the emergence or growth of vegetation in an amount of from 500-1500 g ai/ha (e.g., from 600-1400 g ai/ha, from 700-1300 g ai/ha, from 800-1250 g ai/ha, or from 900-1200 g ai/ha).

Herbicidal Mixtures or Combinations

The (a) penoxsulam or an agriculturally acceptable salt thereof is mixed with or applied in combination with (b) pethoxamid or an agriculturally acceptable salt thereof in an amount sufficient to induce a synergistic herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X * Y}{100}$$

wherein
X=effect in percent using (a) penoxsulam or an agriculturally acceptable salt thereof at an application rate a;
Y=effect in percent using (b) pethoxamid or an agriculturally acceptable salt thereof at an application rate b;
E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of penoxsulam or an agriculturally acceptable salt thereof and pethoxamid or an agriculturally acceptable salt thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the weight ratio of (a) penoxsulam or agriculturally acceptable salt thereof to (b) pethoxamid or an agriculturally acceptable salt thereof that is sufficient to induce a synergistic herbicidal effect is at least 1:500 (e.g., at least 1:480, at least 1:460, at least 1:440, at least 1:420, at least 1:400, at least 1:380, at least 1:360, at least 1:340, at least 1:320, at least 1:300, at least 1:280, at least 1:260, at least 1:240, at least 1:220, at least 1:200, at least 1:190, at least 1:180, at least 1:170, at least 1:160, at least 1:150, at least 1:140, at least 1:130, at least 1:120, at least 1:110, at least 1:100, at least 1:95, at least 1:90, at least 1:85, at least 1:80, at least 1:75, at least 1:70, at least 1:65, at least 1:60, at least 1:55, at least 1:50, at least 1:48, at least 1:46, at least 1:44, at least 1:42, at least 1:40, at least 1:38, at least 1:36, at least 1:34, at least 1:32, at least 1:30, at least 1:28, at least 1:26, at least 1:24, at least 1:22, at least 1:20 at least 1:18, at least 1:16, at least 1:15, at least 1:14, at least 1:13, at least 1:12, or at least 1:11). In some embodiments, the weight ratio of (a) to (b) that is sufficient to induce a synergistic herbicidal effect is 1:10 or less (e.g., 1:11 or less, 1:12 or less, 1:13 or less, 1:14 or less, 1:15 or less, 1:17 or less, 1:19 or less, 1:20 or less, 1:22 or less, 1:24 or less, 1:26 or less, 1:28 or less, 1:30 or less, 1:32 or less, 1:34 or less, 1:36 or less, 1:38 or less, 1:40 or less, 1:42 or less, 1:44 or less, 1:46 or less, 1:48 or less, 1:50 or less, 1:55 or less, 1:60 or less, 1:65 or less, 1:70 or less, 1:75 or less, 1:80 or less, 1:85 or less, 1:90 or less, 1:95 or less, 1:100 or less, 1:110 or less, 1:120 or less, 1:130 or less, 1:140 or less, 1:150 or less, 1:160 or less, 1:170 or less, 1:180 or less, 1:190 or less, 1:200 or less, 1:210 or less, 1:230 or less, 1:250 or less, 1:270 or less, 1:290 or less, 1:310 or less, 1:330 or less, 1:350 or less, 1:370 or less, 1:390 or less, 1:410 or less, 1:430 or less, 1:450 or less, 1:470 or less, or 1:490 or less).

The weight ratio of (a) penoxsulam or agriculturally acceptable salt thereof to (b) pethoxamid or an agriculturally acceptable salt thereof that is sufficient to induce a synergistic herbicidal effect can range from any of the minimum ratios described above to any of the maximum values described above. In some embodiments, the weight ratio of (a) penoxsulam or agriculturally acceptable salt thereof to (b) pethoxamid or an agriculturally acceptable salt thereof that is sufficient to induce a synergistic herbicidal effect is from 1:500 to 1:10 (e.g., from 1:450 to 1:20, from 1:400 to 1:30, from 1:350 to 1:40, from 1:300 to 1:50, from 1:275 to 1:60, from 1:250 to 1:65, from 1:245 to 1:70, from 1:240 to 1:100, or from 1:240 to 1:120).

Formulations

The present disclosure also relates to formulations of the compositions and methods disclosed herein. In some embodiments, the formulation can be in the form of a single package formulation including both (a) penoxsulam or an agriculturally acceptable salt thereof and (b) pethoxamid or an agriculturally acceptable salt thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) penoxsulam or an agriculturally acceptable salt thereof and/or (b) pethoxamid or an agriculturally acceptable salt thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the penoxsulam or agriculturally acceptable salt thereof. In some embodiments, the additive is premixed with the pethoxamid or agriculturally acceptable salt thereof. In some embodiments, the additive is premixed with the penoxsulam or agriculturally acceptable salt thereof and the pethoxamid or agriculturally acceptable salt thereof.

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acifluorfen, aclonifen, acrolein, alachlor, allidochlor, alloxydim, allyl alcohol, alorac, ametryn, ametryn, amibuzin, amicarbazone, amidosulfuron, aminocyclopyrachlor, 4-aminopicolinic acid based herbicides, such as halauxifen, halauxifen-methyl, and those described in U.S. Pat. Nos. 7,314,849 and 7,432,227 to Balko, et al., aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bialaphos, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, fluoroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, pentachlorophenol, pentanochlor, pentoxazone, perfluidone, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and amines, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers, and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix. In certain embodiments, the additional pesticide includes mesotrione, or an agriculturally acceptable salt thereof.

In some embodiments, the penoxsulam or an agriculturally acceptable salt thereof is provided in a premixed formulation with an additional pesticide. In some embodiments, the penoxsulam or an agriculturally acceptable salt thereof is premixed with, cyhalofop-butyl, oxyfluorfen, triclopyr, or combinations thereof. Exemplary premixes of penoxsulam or an agriculturally acceptable salt or ester thereof and an additive that are or have been commercially available include, but are not limited to, CLINTON® (a premix incorporating cyhalofop-butyl by Dow AgroSciences LLC), REBELEX® (a premix incorporating cyhalofop-butyl by Dow AgroSciences LLC), PINDAR GT® (a premix incorporating oxyfluorfen by Dow AgroSciences LLC), and GRASP XTRA (a premix incorporating triclopyr by Dow AgroSciences LLC).

In some embodiments, the pethoxamid or an agriculturally acceptable salt thereof is provided in a premixed formulation with an additional pesticide.

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)) or less, nonylphenol ethoxylate or less, benzylcocoalkyldimethyl quaternary ammonium salt or less, blend of petroleum hydrocarbon, alkyl esters, organic acid, and anionic surfactant or less, $C_9$-$C_{11}$ alkylpolyglycoside or less, phosphate alcohol ethoxylate or less, natural primary alcohol ($C_{12}$-$C_{16}$) ethoxylate or less, di-sec-butylphenol EO-PO block copolymer or less, polysiloxane-methyl cap or less, nonylphenol ethoxylate+urea ammonium nitrate or less, emulsified methylated seed oil or less, tridecyl alcohol (synthetic) ethoxylate (8 EO) or less, tallow amine ethoxylate (15 EO) or less, and PEG (400) dioleate-99.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamin B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to NMR spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to nuclear magnetic resonance (NMR) spectrometry.

Methods of Application

The compositions disclosed herein can be applied in any known technique for applying herbicides. Exemplary application techniques include, but are not limited to, spraying, atomizing, dusting, spreading, or direct application. The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation or the crop) or post-emergence (i.e., during and/or after emergence of the undesirable vegetation or the crop).

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, corn (maize), sorghum and cereal crops. In some embodiments, the undesirable vegetation is controlled in a row crop.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions described herein and other complementary herbicides are applied at the same time, either as a combination formulation or as a tank mix, or as sequential applications.

The herbicidal compositions prepared disclosed herein are effective against a variety of types of undesirable vegetation. In some embodiments, the compositions disclosed herein can be used for controlling broadleaf weeds, grass weeds, sedge weeds, and combinations thereof.

In some embodiments, the methods provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wildproso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carona* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morning glory, IAQTA), *Ipomoea hederacea* (L.) Jacq. (ivyleaf morningglory, IPOHE), *Ipomoea lacunosa* L. (white morningglory, IPOLA), *Kickxia elantine* (canker root, KICEL), *Lactuca serriola* L./Torn. (prickly lettuce, LACSE), *Mercurialis annua* (annual mercury, MERAN), *Polygonum persicaria* L. (ladysthumb, POLPE), *Portulaca oleracea* L. (common purslane, POROL), *Sida spinosa* L. (prickly *sida*, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (*kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compositions and methods provided herein are utilized to control undesirable vegetation consisting of grass, broadleaf and sedge weeds. In certain embodiments, the compositions and methods provided herein are utilized to control undesirable grass, broadleaf and sedge vegetation including but not limited to common ragweed (AMBEL), common lamb's quarters (CHEAL), barnyard grass (ECHCG), canker root (KICEL), annual mercury (MERAN), common cocklebur (XANST), ladysthumb (POLPE), or combinations thereof.

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below.

EXAMPLES

Evaluation of Pre-Emergence Applications of Penoxsulam and Pethoxamid for Synergistic Weed Control Field trials were conducted with applications made in the area of naturally occurring weed populations in Germany, France, Hungary and Italy. The soil was treated prior to the emergence of target plants. All treatments were applied using a randomized complete block trial design, plots 3 meters (m) wide by 8-10 m long, with 3 replications per treatment.

Treatments consisted of penoxsulam and pethoxamid, applied alone and in combination. Spray solutions were prepared using an appropriate amount of dilution to treat the area of the plots based on use rates and water volumes necessary based on a per hectacre basis. Spray solutions were prepared and applied with the specified active ingredients in single and two-way combinations to be able to perform Colby synergy calculations. Formulated products were applied to the soil with a backpack or bicycle compressed air sprayer equipped with flat fas nozzles calibrated to deliver from 200 to 300 L/ha at a normal spray height above the solid, at spray pressures ranging from 210 to 350 kilopascals (kPa).

The Bayer codes of the target plants are provided in Table 1 below. The treated plots and control plots were rated blind at various intervals after application. Ratings were based on a scale of 0-100%, as discussed above, wherein 0% indicates no control of the undesired vegetation and 100% indicates complete control of the undesired vegetation.

Colby's equation was used to determine the herbicidal effects expected from the mixtures, as described above. The results were measured at the evaluation intervals provided in Table 1 after the first application of the compositions. The trials exhibited unexpected synergy, and those results were found statistically significant under the p-value test. The herbicide tank mix combinations tested, application rates and ratios employed, plant species tested, and results are given below.

TABLE 1

Synergistic Weed Control from Applications of Penoxsulam + Pethoxamid.

| | | Penoxsulam | | Pethoxamid | | Combination | |
|---|---|---|---|---|---|---|---|
| | | | | | | Measured | Colby predicted |
| Weed Bayer | Evaluation Interval | g ai/ha | Mean % weed control | g ai/ha | Mean % weed control | mean % weed control | mean % weed control |
| CHEAL | 46 days | 5 | 43.33 | 1200 | 16.67 | 84 | 52.58 |
| CHEAL | 29 days | 5 | 95 | 1200 | 0 | 100 | 95 |
| KICEL | 29 days | 10 | 20 | 1200 | 0 | 90 | 20 |
| MERAN | 29 days | 10 | 36.67 | 1200 | 0 | 70 | 36.67 |
| CHEAL | 14 days | 5 | 26.67 | 1200 | 26.67 | 63.33 | 46.33 |
| AMBEL | 14 days | 10 | 78.33 | 1200 | 33.33 | 98.67 | 85.5 |
| AMBEL | 14 days | 5 | 50 | 1200 | 33.33 | 93.67 | 66.67 |
| ECHCG | 28 days | 10 | 76.67 | 1200 | 33.33 | 91.67 | 84.5 |
| CHEAL | 28 days | 5 | 13.33 | 1200 | 6.67 | 50 | 19 |
| AMBEL | 28 days | 10 | 66.67 | 1200 | 13.33 | 98 | 71 |
| AMBEL | 28 days | 5 | 33.33 | 1200 | 13.33 | 90.33 | 42.33 |
| XANST | 28 days | 5 | 20 | 1200 | 3.33 | 53.33 | 22.33 |
| ECHCG | 58 days | 10 | 63.33 | 1200 | 16.67 | 86.33 | 69.33 |
| ECHCG | 58 days | 5 | 20 | 1200 | 16.67 | 46.67 | 33.33 |

TABLE 1-continued

Synergistic Weed Control from Applications of Penoxsulam + Pethoxamid.

| | | Penoxsulam | | Pethoxamid | | Combination | |
|---|---|---|---|---|---|---|---|
| | | | | | | Measured | Colby predicted |
| Weed Bayer | Evaluation Interval | g ai/ha | Mean % weed control | g ai/ha | Mean % weed control | mean % weed control | mean % weed control |
| AMBEL | 58 days | 10 | 66.67 | 1200 | 13.33 | 96.67 | 71 |
| AMBEL | 58 days | 5 | 33.33 | 1200 | 13.33 | 90 | 42.33 |
| XANST | 58 days | 5 | 10 | 1200 | 0 | 43.33 | 10 |
| POLPE | 54 days | 5 | 90 | 1200 | 72.33 | 100 | 97.2 |

AMBEL - *Ambrosia artemisiifolia* L. (common ragweed)
CHEAL - *Chenopodium album* L. (common lambsquarters)
ECHCG - *Echinochloa crus-galli* (L.) P. Beauv. (barnyardgrass)
KICEL - *Kickxia elantine* (canker root)
MERAN - *Mercurialis annua* (annual mercury)
POLPE - *Polygonum persicaria* L. (ladysthumb)
XANST - *Xanthium strumarium* L. (common cocklebur)

As shown above, the weed control from the treatments in these trials demonstrated synergistic weed control, with higher measured weed control than would be predicted by the Colby equation.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a synergistic herbicidally effective amount of (a) penoxsulam, or an agriculturally acceptable salt thereof, and (b) pethoxamid, or an agriculturally acceptable salt thereof, wherein the weight ratio of (a) to (b) is from 1:480 to 1:60.

2. The composition of claim 1, wherein the weight ratio of (a) to (b) is from 1:300 to 1:60.

3. The composition of claim 1, wherein the weight ratio of (a) to (b) is from 1:240 to 1:120.

4. The composition of claim 1, wherein the composition is provided as a herbicidal concentrate.

5. A method of controlling undesirable vegetation, the method comprising, applying to vegetation or an area adjacent the vegetation or applying to soil to control the emergence or growth of vegetation a synergistic herbicidally effective amount of (a) penoxsulam, or an agriculturally acceptable salt thereof, and (b) pethoxamid, or an agriculturally acceptable salt thereof, wherein the weight ratio of (a) to (b) is from 1:480 to 1:60.

6. The method of claim 5, wherein (a) and (b) are applied simultaneously.

7. The method of claim 5, wherein (a) and (b) are applied to the soil to control the emergence or growth of undesirable vegetation.

8. The method of claim 5, wherein (a) and (b) are applied post-emergence to the undesirable vegetation to control the growth of the undesirable vegetation.

9. The method of claim 5, wherein the undesirable vegetation is controlled in corn, *sorghum* or cereal crops.

10. The method of claim 5, wherein the undesirable vegetation is controlled in glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) inhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

11. The method of claim 10, wherein the tolerant crop possesses multiple or stacked traits conferring tolerance to multiple herbicides or multiple modes of action.

12. The method of claim 5, wherein the undesirable vegetation comprises a herbicide resistant or tolerant weed.

13. The method of claim 5, wherein the undesirable vegetation includes a broadleaf weed.

14. The method of claim 5, wherein the undesirable vegetation includes a grass weed.

15. The method of claim 5, wherein the undesirable vegetation includes a sedge weed.

16. The method of claim 5, wherein (a) and (b) are applied in a weight ratio of (a) to (b) from 1:300 to 1:60.

17. The method of claim 5, wherein (a) is applied in an amount of from 3-30 g ai/ha.

18. The method of claim 5, wherein (b) is applied in an amount of from 750-1300 g ai/ha.

* * * * *